US010874652B2

(12) United States Patent
Pisconti (10) Patent No.: US 10,874,652 B2
(45) Date of Patent: Dec. 29, 2020

(54) MUSCLE REGENERATION (71) Applicant: The Research Foundation for The State University of New York, Albany, NY (US)

(72) Inventor: Addolorata Pisconti, Liverpool (GB)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 16/300,283

(22) PCT Filed: May 15, 2017

(86) PCT No.: PCT/GB2017/051349
§ 371 (c)(1),
(2) Date: Nov. 9, 2018

(87) PCT Pub. No.: WO2017/194975
PCT Pub. Date: Nov. 16, 2017

(65) Prior Publication Data
US 2019/0134014 A1    May 9, 2019

(30) Foreign Application Priority Data

May 13, 2016   (GB) .................................. 1608453.5
Sep. 13, 2016   (GB) .................................. 1615529.3

(51) Int. Cl.
| A61K 31/444 | (2006.01) |
| A61P 21/00 | (2006.01) |
| A61K 38/00 | (2006.01) |
| A61K 31/505 | (2006.01) |
| A61K 31/222 | (2006.01) |
| A61K 31/26 | (2006.01) |
| A61P 25/14 | (2006.01) |
| A61K 31/00 | (2006.01) |
| A61K 45/06 | (2006.01) |

(52) U.S. Cl.
CPC ............ *A61K 31/444* (2013.01); *A61K 31/00* (2013.01); *A61K 31/222* (2013.01); *A61K 31/26* (2013.01); *A61K 31/505* (2013.01); *A61K 38/005* (2013.01); *A61P 21/00* (2018.01); *A61P 25/14* (2018.01); *A61K 45/06* (2013.01)

(58) Field of Classification Search
CPC ... A61K 31/444; A61K 31/222; A61K 31/505
See application file for complete search history.

(56) References Cited

U.S. PATENT DOCUMENTS

2008/0146585 A1* 6/2008 Moussy ............... A61K 31/421
514/253.1

OTHER PUBLICATIONS

Nussbaum (Bioorganic & Medicinal Chemistry Letters 25 (2015) 4370-4381).*
Arecco N. et al., "Elastase Levels and Activity are Increased in Dystrophic Muscle and Impair Myoblast Cell Survival, Proliferation and Differentiation", Scientific Reports 6(1):1-20 (May 31, 2016).
Henriksen P.A., "The Potential of Neutrophil Elastase Inhibitors as Anti-Inflammatory Therapies", Current Opinion in Hamatology 21(1):23-28 (Jan. 2014).
Kharraz Y. et al., "Understanding the Process of Fibrosis in Duchenne Muscular Dystrophy", BioMed Research International 2014(ID965631):1-11 (Jan. 1, 2014).
Mah J K, "Current and Emerging Treatment Strategies for Duchenne Muscular Dystrophy", Neuropsychiatric Disease and Treatment 2016(12):1795-1807 (May 10, 2016).
Nussbaum F V et al., "Neutrophil Elastase Inhibitors for the Treatment of (Cardio) Pulmonary Diseases: Into Clinical Testing With Pre-Adaptive Pharmacophores", Bioorganic & Medicinal Chemistry Letters 25:4370-4381 (Aug. 20, 2015).
International Search Report dated Aug. 2, 2017 received in International Application No. PCT/GB2017/051349.

* cited by examiner

*Primary Examiner* — Pancham Bakshi
(74) *Attorney, Agent, or Firm* — Scully, Scott, Murphy & Presser, P.C.

(57) ABSTRACT

The invention provides anelastase inhibitor for use in the promotion of muscle regeneration in the treatment of a myopathy, as well as a method for promoting muscle regeneration in a subject with a myopathy, the method comprising providing the subject with a therapeutically effective amount of an elastase inhibitor. Further provided is a pharmaceutical composition comprising anelastase inhibitor for use in the promotion of muscle regeneration in the treatment of a myopathy. Elastase inhibitors may have a protective effect on muscle progenitor cells and their regenerative potential, which aids muscle cell regeneration. By protecting regenerative potential of muscle progenitor cells, elastase inhibitors enable or enhance the grown of new or existing muscle fibres.

9 Claims, 10 Drawing Sheets

MUSCLE REGENERATION

FIELD OF THE INVENTION

The present invention relates to elastase inhibitors for use in the promotion of muscle regeneration in the treatment of a myopathy. The invention also relates to methods of promoting muscle regeneration in the treatment of a myopathy, as well as pharmaceutical compositions comprising an elastase inhibitor for use in the promotion of muscle regeneration in the treatment of a myopathy.

BACKGROUND

Myopathies are a group of neuromuscular disorders associated with muscle weakness due to the dysfunction of muscle fibres. Muscular dystrophies are a subgroup of myopathies, characterised by progressive weakening of the skeletal muscles. The weakening of the skeletal muscle is a result of defects in muscle proteins, which, in some cases, lead to muscle cell death. There are nine major types of muscular dystrophy: Duchenne muscular dystrophy, Becker muscular dystrophy, congenital muscular dystrophy, distal muscular dystrophy, Emery-Dreifuss muscular dystrophy, facioscapulohumeral muscular dystrophy, limb-girdle muscular dystrophy, myotonic muscular dystrophy and oculopharyngeal muscular dystrophy.

Duchenne muscular dystrophy is the most common form of muscular dystrophy. It affects 1 in approximately 3,500 live male births. Duchenne muscular dystrophy is a progressive muscle degenerative disorder characterised by muscle weakness and progressive muscle loss. In Duchenne muscular dystrophy most of the muscles of the body are affected leading to loss of independent ambulation by approximately the age of 12, cardiomyopathy by the age of 18 and subsequent loss of respiratory capacity in the second decade of life.

The molecular cause of Duchenne muscular dystrophy is the lack of the cytoskeletal protein dystrophin, which links the cell cytoskeleton to the extracellular matrix and therefore distributes linearly the force generated during muscle fibre contraction. In the absence of dystrophin, the muscle fibres become very sensitive to contraction-induced stress and are easily damaged. This causes the continuous formation of foci of injury in dystrophic muscle that are initially repaired through the regenerative activity of the local muscle stem cells. However, for unknown reasons, the muscle stem cell regenerative potential is exhausted early in life in patients with Duchenne muscular dystrophy leading to loss of muscle regeneration upon disease-induced injury and replacement of the damaged muscle tissue with scar tissue (fibrosis). Over time the muscle tissue is lost leading to muscle weakness and eventually complete loss of muscle function.

To date there is no cure or effective treatment for Duchenne muscular dystrophy. The management is currently based on the use of corticosteroids, which delay loss of ambulation and cardiomyopathy but also cause significant side effects often poorly tolerated by children and teenagers with Duchenne muscular dystrophy.

It is an aim of certain embodiments of the invention to obviate or mitigate at least some of the problems noted above. It is an aim of certain embodiments of the invention to provide agents for use in the promotion of muscle regeneration in the treatment of myopathies, such as muscular dystrophy. It is an aim of certain embodiments of the invention to provide methods of treatment for use in the promotion of muscle regeneration in the treatment of myopathies, such as muscular dystrophy. It is an aim of certain embodiments of the invention to provide pharmaceutical compositions for use in the promotion of muscle regeneration in the treatment of myopathies, such as muscular dystrophy.

BRIEF SUMMARY OF THE DISCLOSURE

In a first aspect, the invention provides an elastase inhibitor for use in the promotion of muscle regeneration in the treatment of a myopathy.

In a second aspect, the invention provides a method for promoting muscle regeneration in a subject with a myopathy, the method comprising providing the subject with a therapeutically effective amount of an elastase inhibitor.

In a third aspect, the invention provides a pharmaceutical composition comprising an elastase inhibitor for use in the promotion of muscle regeneration in the treatment of a myopathy.

In a fourth aspect, the invention provides a method of determining effectiveness of a treatment in a subject with a myopathy, the method comprising the steps of:
  measuring elastase activity in a sample from the subject;
  comparing the elastase activity in the subject's sample to a reference value, and
  thereby determining the effectiveness of the treatment.

It will be appreciated that elastase inhibitors for use according to the first aspect of the invention may be incorporated into pharmaceutical compositions suitable for administration to a subject requiring promotion of muscle regeneration in the treatment of a myopathy. Such pharmaceutical compositions may afford suitable means by which a therapeutically effective amount of an elastase inhibitor is provided to a subject in the method of treatment according to the second aspect of the invention. Accordingly, it will be recognised that, except where the context requires otherwise, embodiments described in respect of one aspect of the invention will also be applicable to the other two aspects.

It will also be appreciated that in the context of the fourth aspect of the invention, the treatment the effectiveness of which is being determined may employ an elastase inhibitor for use according to the first aspect of the invention, or a pharmaceutical composition for use according to the third aspect of the invention, or may be a method of treatment in accordance with the second aspect of the invention.

BRIEF DESCRIPTION OF THE DRAWINGS

Embodiments of the invention are further described herein with reference to the accompanying drawings, in which.

DETAILED DESCRIPTION

The inventors have surprisingly found that increased elastase levels, and especially increased neutrophil elastase levels, may impair muscle regeneration. Without wishing to be bound by any particular hypothesis, the inventors believe that increased elastase levels damage the extracellular matrix which may result in a loss of muscle progenitor cell (such as such as satellite cell, pericytes, myoendothelial cell, side population cell, mesenchymal stem cell or myoblast cell) regenerative potential.

It is established in the scientific literature that loss of muscle progenitor cell regenerative potential impairs the capacity of muscle tissue to regenerate. The loss of muscle progenitor cell regenerative potential may be therefore associated with the progressive loss of muscle strength and muscle mass typically observed in patients diagnosed with a myopathy, in particular muscle dystrophy such as Duchenne muscle dystrophy.

The inventors have unexpectedly found that elastase inhibitors may have a protective effect on muscle progenitor cells and their regenerative potential, which aids muscle cell regeneration. This surprising finding gives rise to a new approach to the treatment of muscular dystrophies and other myopathies.

Elastase Inhibitor

In the context of the present invention, the term "elastase inhibitor" refers to any compound capable of reducing elastase enzyme activity, and thereby promoting muscle regeneration. Elastases are proteases which cleave the extracellular protein elastin and other extracellular proteins such as laminins, collagens and fibronectin. Accordingly, the term "elastase inhibitor" encompasses any compound capable of reducing the ability of an elastase enzyme to cleave its protein substrate.

Several methods for measuring elastase enzyme activity are known in the art. Merely by way of example, elastase activity can be determined by measuring the fluorescence emitted by a fluorigenic peptide such as MeOSuc-Ala-Ala-Pro-Val-AFC or Suc-Ala-Ala-Ala-AMC. Fluorescence may be measured, for example, using a plate reader. Other suitable assays for measuring elastase activity will be known to the skilled person. These may include measuring the product generated by incubation with a fluorescently labelled peptide such as 5-FAM-Arg-Glu-Ala-Val-Val-Tyr or 5-FAM-Ala-Ala-Ala-Phe-Tyr-Asp using an instrument that detects the size of the fluorescently labelled probe.

In a suitable embodiment, an elastase inhibitor may reduce elastase enzyme activity by at least 30%, at least 40%, at least 50%, at least 60%, or at least 70%, or more compared to normal elastase enzyme activity. Suitably, an elastase inhibitor may reduce elastase enzyme activity by at least 75%, at least 80%, at least 85%, at least 90%, at least 95% or more compared to normal elastase enzyme activity. Normal elastase enzyme activity refers to the activity of an elastase enzyme without the presence of an elastase inhibitor.

A suitable elastase enzyme inhibitor may reduce the activity of an elastase enzyme either ex vivo or in vivo.

In a suitable embodiment term "elastase inhibitor" encompasses any compound capable of reducing the activity of one or more elastase enzymes selected from the group consisting of: neutrophil elastase, macrophage metalloelastase, chymotrypsin-like elastase family, member 1; chymotrypsin-like elastase family, member 2A; chymotrypsin-like elastase family, member 2B; chymotrypsin-like elastase family, member 3A; chymotrypsin-like elastase family, member 3B; and chymotrypsin C (caldecrin).

Alternatively, a suitable elastase enzyme inhibitor may specifically inhibit the activity of neutrophil elastase enzyme. The neutrophil elastase enzyme is the enzyme encoded by the gene ELANE.

In a suitable embodiment the elastase inhibitor is an extracellular elastase inhibitor. In a particularly suitable embodiment the extracellular elastase inhibitor is an extracellular inhibitor of neutrophil elastase.

An extracellular elastase inhibitor is any compound capable of reducing the activity of an elastase enzyme occurring outside the cell. Such elastase inhibitors may prevent the degradation of the extracellular matrix caused by increased levels and/or increased activity of extracellular elastase enzymes.

Suitably, an elastase inhibitor may be provided extracellularly at a site of a myopathy. In this context, an extracellular elastase inhibitor may be one that is unable to cross the cell membrane, and thereby enter a cell. It will be appreciated that extracellular inhibitors of elastase activity of this sort will not inhibit intracellular elastase activity if provided extracellularly at a site of a myopathy requiring treatment (for example, if provided systemically).

A suitable elastase inhibitor may be selected from the group consisting of: Alvelestat, Elastatinal, Sivelestat, BAY85-8501, BAY-678, Freselestat, AZD9819, GW-311616A, POL6014, SSR 69071, GW475151, ICI 200, 880 and AX-9657, Midesteine, 1-(3-methylbenzoyl)-1H-indazole-3-carbonitrile, Elastase inhibitor II, Elastase inhibitor III, Elastase inhibitor V, N-(Methoxysuccinyl)-Ala-Ala-Pro-Val-chloromethyl ketone, 1,4-diarylpyrimidopyridazinyldione or a derivative thereof, 2-pyrazinone or a derivative thereof, 2-pyridone or a derivative thereof, pyridyl-3-yl-benzo[d][1,3]oxazin-4-one or a derivative thereof, 3,4,6,7-tetrahydro-1H-pyrrolo[3,4-d]pyrimidine-2,5-dione or derivative thereof, 4-(4-Cyano-2-thioaryl)-dihydropyrimidone or a derivative thereof, 4-(4-cyanophenyl)-1-(3-trifluoromethylphenyl)-3,4,6,7-tetrahydro-1H-pyrrolo[3,4-d]pyrimidine-2,5-dione or a derivative thereof, Azetidine-2,4-dione or a derivative thereof, Benzoxazinone or a derivative thereof, Dihydropyrimidone or a derivative thereof, functionalized N-amino-4-imidazolidinone, N-Benzoyl pyrazole or a derivative thereof, Tetrazolopyrimidine or a derivative thereof, Serpinb1, Elafin, Alpha-1-antitrypsin, Protein AMBP, Antileukoproteinase, Eppin and Alpha-2-macroglobulin.

More suitably, the elastase inhibitor may be selected from the group consisting of: Alvelestat, Elastatinal, Sivelestat, BAY85-8501, BAY-678, Freselestat and AZD9819.

A suitable elastase inhibitor may be exogenous or endogenous.

For the purpose of the present invention, an exogenous elastase inhibitor is one which is not naturally occurring in humans. Merely by way of example, an exogenous elastase inhibitor may be a synthetic small molecule, or an elastase inhibitor which is naturally found in bacteria (or other non-human organisms). An example of an elastase inhibitor which is naturally found in bacteria is Elastatinal.

For the purpose of the present invention, an endogenous elastase inhibitor is one which is naturally occurring in humans. However, it will be appreciated that an endogenous elastase inhibitor may be synthetically produced. Such a synthetically produced endogenous elastase inhibitor is one which has the same chemical structure as any elastase inhibitor that naturally occurs in humans.

Endogenous elastase inhibitors may be particularly useful in the context of gene therapy. Such elastase inhibitors may be provided to the subject either directly or indirectly. Direct provision of an endogenous elastase inhibitor may involve administering to the subject the endogenous elastase inhibitor itself.

Merely by way of example, indirect provision of an endogenous elastase inhibitor may involve administering a compound which will result in increased expression of an endogenous elastase inhibitor in the subject. Alternatively, the indirect provision of an endogenous elastase inhibitor may involve administering a nucleic acid which encodes an endogenous elastase inhibitor.

Promotion of Muscle Regeneration

The first and second aspects of the invention respectively relate to medical uses and methods of treatment for the promotion of muscle regeneration in the treatment of myopathies. Such a promotion of muscle regeneration may be due to the ability of elastase inhibitors to protect muscle progenitor cell regenerative potential. In this context, the promotion of muscle regeneration refers to any clinical improvement in muscle function, which may be demonstrated by increased muscle strength, increased muscle mass, reduced pseudohypertrophy and/or reduced muscle atrophy. The clinical improvement may be compared to the state that otherwise occurs in an untreated myopathy.

Accordingly, in one embodiment muscle regeneration may be considered to be promoted if the muscle strength and/or muscle mass is increased by at least 5%, at least 10%, at least 20%, at least 30%, at least 40%, at least 50%, at least 60%, at least 70% or more as compared to control or the subjects own muscle strength and/or muscle mass prior to treatment. Methods for testing muscle strength may include a walk or run test, but other methods will be known to the skilled person. Methods for testing muscle mass include, for example, determining 24 hour urinary creatinine levels, or body scanning using methods such as Dual-Energy X-Ray Absorptiometry (DEXA), Total Body Potassium (TBK), Magnetic Resonance Imaging (MRI), Total Body Electrical Conductivity (TOBEC), and Computed Tomography (CT)

In a suitable embodiment, muscle regeneration may be considered to be promoted if pseudohypertrophy and/or muscle atrophy is decreased by at least 5%, at least 10%, at least 20%, at least 30%, at least 40%, at least 50%, at least 60%, at least 70% or more as compared to control or pseudohypertrophy and/or muscle atrophy observed in the subject prior to treatment. A decrease in pseudohypertrophy may be observed by a reduction in size of the calf muscle. A decrease in muscle atrophy may, for example, be determined histologically. Other methods for assessing pseudohypertrophy and/or muscle atrophy will be known to the skilled person.

The ability of elastase inhibitors to promote muscle regeneration in the treatment of myopathies is based on the inventor's surprising finding that elastase inhibitors have a protective effect on the regenerative potential of muscle progenitor cells associated with myopathies.

The term "muscle progenitor cells" as used herein, refers to cells selected from the group consisting of: satellite cells, pericytes, myoendothelial cells, side population cells, mesenchymal stem cells, and myoblasts. It will be appreciated that references to muscle progenitor cells within the present disclosure may be interpreted as referring to individual populations of such cells (for example solely satellite cells or solely myoblast cells), or to combinations of two, three, four, five, or six of these cell types.

Such a protective effect on muscle progenitor cells in subjects with impaired muscle regeneration due to a myopathy such as Duchenne muscular dystrophy, may result in an increase in muscle progenitor cells. Thus, muscle regeneration may be considered to be promoted if the number of muscle progenitor cells has increased by at least 5%, at least 10%, at least 20%, at least 30%, at least 40%, at least 50%, at least 60%, at least 70% or more as compared to the number of muscle progenitor cells in a relevant control (such as a sample from the same subject prior to treatment).

Suitably the elastase inhibitors achieve their therapeutic effect through promoting muscle regeneration by protecting muscle progenitor cells. The inventors believe that by protecting muscle progenitor cell regenerative potential, elastase inhibitors enable or enhance the growth of new or existing muscle fibres, particularly in individuals diagnosed with a myopathy. Accordingly, muscle regeneration may be considered to be promoted if the number of new muscle fibres is increased by at least 5%, at least 10%, at least 20%, at least 30%, at least 40%, at least 50%, at least 60%, at least 70% or more. Similarly, muscle regeneration may be considered to be promoted if the thickness of existing muscle fibres is increased by at least 5%, at least 10%, at least 20%, at least 30%, at least 40%, at least 50%, at least 60%, at least 70% or more. The number of new muscle fibres, as well as the thickness of existing muscle fibres may, for example, be determined through histological analysis of muscles pre and post exposure to elastase inhibitors. Suitably, muscle regeneration may be considered to be promoted if muscle fibre diameter has increased by at least 5%, at least 10%, at least 20%, at least 30%, at least 40%, at least 50%, at least 60%, at least 70% or more. Muscle fibre diameter may be determined using various methods known to the skilled person, including measuring the minimum Feret diameter or the area of a muscle fibre cross-section.

The inventors believe that the protective effect of elastase inhibitors on muscle progenitor cell regenerative potential may prevent elastase induced loss of muscle fibres. Muscle fibre loss may result from a reduction in the number of muscle progenitor cells, reduction in muscle progenitor cells proliferation (in particular myoblast proliferation), reduction in muscle progenitor cell differentiation (in particular myoblast differentiation), a reduction in myoblast fusion and/or a reduction in myotube growth.

Therefore, in the context of the present invention, the term "promotion of muscle regeneration" is intended to include one or more protective effects on muscle progenitor cells. Such protective effects may be selected from the group consisting of: increased muscle progenitor cell number, increased muscle progenitor cell proliferation, increased muscle progenitor cell differentiation, increased muscle progenitor cell survival, increased myoblast fusion, and/or increased myotube growth.

In one embodiment, muscle regeneration may be considered to be promoted if muscle progenitor cell number, muscle progenitor cell proliferation, muscle progenitor cell differentiation, muscle progenitor cell survival, myoblast fusion and/or myotube growth is increased by at least 5%, at least 10%, at least 20%, at least 30%, at least 40%, at least 50%, at least 60%, at least 70% or more.

In one embodiment, muscle regeneration may be considered to be promoted if muscle fibrosis is reduced. Suitably, muscle fibrosis may be reduced by at least 5%, at least 10%, at least 20%, at least 30%, at least 40%, at least 50%, at least 60%, at least 70% or more. More suitably, muscle regeneration may be considered to be promoted if muscle fibrosis is reduced by at least 30%. The skilled person will appreciate that there are various methods for determining muscle fibrosis. Such methods may include a muscle biopsy to measure the extent of muscle fibrosis (for example pre- and post-treatment)

A Subject

The term "subject" as used herein, refers to any individual who may benefit from the promotion of muscle regeneration in the treatment of a myopathy. The subject may be a human subject. Suitably, the human subject may be a child.

An individual who may benefit from the promotion of muscle regeneration may have symptoms associated with a myopathy, such as muscle weakness and/or reduced muscle mass. Alternatively, the subject may be asymptomatic but at risk of developing such symptoms. Symptoms associated with muscle weakness and/or reduced muscle mass include, but are not limited to a difficulty in walking, difficulty in running, difficulty in standing up and/or difficulty in breathing.

Disorders particularly associated with muscle weakness and/or impaired muscle regeneration include myopathies, in particular myopathies associated with muscle inflammation. Such myopathies are characterized by increased infiltration of white blood cells (in particular neutrophils) in the muscles. By way of example, a myopathy associated with muscle inflammation may be determined by histological analysis (such as haematoxylin and eosin staining) of a muscle biopsy. Merely by way of example, myopathies associated with muscle inflammation may be selected from the group consisting of polymyositis, dermatomyositis, inclusion body myositis, congenital inflammatory myopathy and muscular dystrophy.

Accordingly, a subject may be any individual diagnosed with, or at risk of developing a myopathy. Suitably the subject may be an individual diagnosed with, or at risk of developing a myopathy associated with muscle inflammation. In particular, the subject may be diagnosed with, or at risk of developing polymyositis, dermatomyositis, inclusion body myositis, congenital inflammatory myopathy or a muscular dystrophy. A suitably muscular dystrophy may be selected from the group consisting of: Duchenne muscular dystrophy, Becker muscular dystrophy, congenital muscular dystrophy, distal muscular dystrophy, Emery-Dreifuss muscular dystrophy, facioscapulohumeral muscular dystrophy, limb-girdle muscular dystrophy, myotonic muscular dystrophy and oculopharyngeal muscular dystrophy. Suitably, the subject may be diagnosed with, or at risk of developing Duchenne muscular dystrophy.

In a suitable embodiment, a subject may be considered at risk, for example, due to a known predisposition, such as the presence of a mutation (for example the DMD gene) and/or a familial history. Suitably, a subject at risk of developing symptoms associated with impaired muscle regeneration may be asymptomatic.

Treatment of Myopathies (Such as Muscular Dystrophy)

The medical uses and methods of treatment of the first and second aspects of the invention are useful in the treatment of myopathies. In a suitable embodiment, the uses and methods of the first and second aspects of the invention may be employed in the treatment of muscular dystrophy. Suitably, the muscular dystrophy may be Duchenne muscular dystrophy.

The term "treatment" as used herein refers to an intervention which prevents the progression, or reduces partially or completely the clinical symptoms associated with a myopathy, such as muscular dystrophy, in a subject. Accordingly, the term "treatment" encompasses not only the therapeutic use of elastase inhibitors in a subject with the symptoms of a myopathy, such as muscular dystrophy, but also the use of elastase inhibitors in the treatment of a subject who does not exhibit the symptoms of the myopathy. Such uses may be of particular relevance to an asymptomatic subject known to carry a mutation which increases the subject's likelihood of developing a myopathy, such as muscular dystrophy.

A Therapeutically Effective Amount

The term "a therapeutically effective amount" as used herein, refers to an amount of elastase inhibitor, that when provided to the subject with a myopathy, is sufficient to promote muscle regeneration in the subject. Merely by way of example promotion of muscle regeneration may be demonstrated by a clinical improvement of symptoms associated with reduced muscle regeneration. Other ways in which promotion of muscle regeneration may be demonstrated are considered elsewhere in this specification. By way of example, an improvement in symptoms may be demonstrated by increased muscle strength and/or increased muscle mass.

Additionally or alternatively, promotion of muscle regeneration may be demonstrated by an improvement in muscle pathology. Suitably, an improvement in muscle pathology may be demonstrated by a decrease in muscle fibrosis, a decrease in muscle inflammation and an increase in muscle progenitor cell number, increase in muscle progenitor cell proliferation, increase in muscle progenitor cell differentiation, increase in myoblast fusion, increase in myotube growth, and/or increase in muscle progenitor cell survival.

It will be appreciated that the therapeutically effective amount may vary depending on various factors, including the type of elastase inhibitor. Different types of elastase inhibitors will have a different half-life and/or bioavailability, which may alter the therapeutically effective amount.

The therapeutically effective amount may also vary depending on the subject's age, weight and/or gender.

By way of example, a therapeutically effective amount of the elastase inhibitor Sivelestat may be between 1 and 10 mg/kg/day, suitably between 3 and 7 mg/kg/day, more suitable approximately 5 mg/kg/day. By way of example, a therapeutically effective amount of the elastase inhibitor Depelestat may be between 0.5 and 7 mg/kg/day, suitably between 1.5 and 5 mg/kg/day, more suitably approximately 3 mg/kg/day. By way of example, a therapeutically effective amount of the elastase inhibitor Alvelestat may be between 10 and 150 mg/day, suitably 50 and 100 mg/day, more suitably approximately 60 mg/day.

Determining Effectiveness

The fourth aspect is based on the inventors' surprising finding that subjects with a myopathy, in particular with muscular dystrophy such as Duchenne muscular dystrophy, may have higher levels of elastase activity as compared to individuals without such a disease. The inventors believe that this finding may be of particular utility in determining or monitoring the effectiveness of a treatment in a subject with a myopathy.

Accordingly, the fourth aspect relates to a method of determining the effectiveness of a treatment in a subject with a myopathy, the method comprising the steps of:
  measuring elastase activity in a sample from the subject;
  comparing the elastase activity in the subject's sample to a reference value, and
  thereby determining the effectiveness of the treatment.

It will be appreciated that the reference value may be based upon the elastase activity measured either in one or more samples from a control individual(s), or in one or more samples from a subject(s) diagnosed with a myopathy and who did not receive treatment.

In one embodiment, the reference value is based upon the elastase activity measured in one or more samples from control individual(s). In such an embodiment, if the elastase activity measured in a sample from a subject treated for a myopathy approximates the elastase activity measured in a sample(s) from the control individual(s), it provides an indication that the treatment is effective.

By the same token, if the elastase activity measured in a sample from a subject treated for a myopathy does not approximate the elastase activity measured in a sample from a control individual, it may be an indication that the treatment is not effective. In the context of the present disclosure the term "approximates" may be taken as referring to elastase activity which is within 0.5-fold or less, 0.4-fold or less, 0.3-fold or less, 0.2-fold or less, 0.1-fold or less, or 0.05-fold or less, from the reference value.

In another embodiment, the reference value is based upon the elastase activity measured in a sample(s) from an individual(s) with a myopathy who has not received treatment. Suitably, the individual with a myopathy may be the subject themselves prior to receiving treatment. In such an embodiment, if the elastase activity measured in a sample from a subject treated for a myopathy approximates the elastase activity measured in a sample from an individual with a myopathy, it may be an indication that the treatment is not effective.

By the same token, if the elastase activity measured in the sample from the subject treated for a myopathy is lower than the elastase activity measured in the sample from an individual with a myopathy, it may be an indication that the treatment is effective. It will be appreciated that any reduction in elastase activity as compared to a reference value based upon elastase activity in a sample from an individual with a myopathy may be an indication that the treatment is effective. Suitably, elastase activity that is at least 0.05-fold, at least 0.1-fold, at least 0.2-fold, at least 0.3-fold, at least 0.4-fold, at least 0.5-fold or more, lower than the reference value, may be an indication that the treatment is effective.

Methods for measuring elastase activity will be known to the skilled person. By way of example, elastase activity may be measured with the use of the fluorigenic peptide Suc-Ala-Ala-Ala-AMC as further explained in the Examples section.

In the context of the present disclosure, the term sample refers to any suitable sample that provides an indication as to the elastase activity in the subject. The sample may be a solid sample or a body fluid sample.

Suitably, the sample may be a fluid sample selected from the group consisting of: a blood sample (for example, a whole blood sample, a blood plasma sample, or a serum sample) and a urine sample. More suitably, the sample is a serum sample.

A suitable solid sample may be a muscle biopsy.

A Pharmaceutical Composition

In one embodiment the pharmaceutical composition may comprise an elastase inhibitor and a pharmaceutically acceptable carrier. Suitably, the pharmaceutical composition may comprise any elastase inhibitor disclosed herein. More suitably, the elastase inhibitor may be selected from the group consisting of: Alvelestat, Sivelestat, BAY85-8501, BAY-678, Freselestat and AZD9819.

The "term pharmaceutically acceptable carrier" as used herein refers to any suitable diluent, excipient, or a combination thereof, suitable for administration into a subject. A pharmaceutically acceptable carrier may be an organic or inorganic substance, which facilities the delivery of an elastase inhibitor to the subject.

In a suitable embodiment, a pharmaceutical composition of the invention may further comprise a pharmaceutically acceptable concentration of salt, buffering agents, and compatible carriers. The compositions may also include antioxidants and/or preservatives. Suitable antioxidants may be selected from the group consisting of: mentioned thiol derivatives (e.g. thioglycerol, cysteine, acetylcysteine, cystine, dithioerythreitol, dithiothreitol, glutathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiareticacid. Suitable preservatives may for instance be phenol, chlorobutanol, benzylalcohol, methyl paraben, propyl paraben, benzalkonium chloride and cetylpyridinium chloride.

The pharmaceutical composition of the present invention may be for administration to the subject via any suitable route. A suitable route of administration may be selected from the group consisting of: oral, intramuscular, intravenous, intraperitoneal and subcutaneous. Other methods for administering pharmaceutical compositions will be known to the skilled in the art.

In one embodiment, the pharmaceutical composition of the present invention is for oral administration. Suitable oral administration forms include solid dosage forms, such as capsules, tablets, powders and granules. In such solid dosage forms, the elastase inhibitor may be mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules and tablets, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations may contain a dissolution aid. The dissolution aid is not limited as to its identity so long as it is pharmaceutically acceptable. Examples include non-ionic surface agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface agents, such as betaines and aminocarboxylic acid salts. Pharmaceutical compositions of the invention, comprising an elastase inhibitor may also be in microencapsulated form, if appropriate, with one or more of the above-mentioned excipients.

In one embodiment, the pharmaceutical composition is for administration in liquid dosage form. Liquid dosage forms for oral administration include pharmaceutically acceptable emulsions, solutions, suspensions, syrups and elixirs. In addition to the elastase inhibitor, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavouring and perfuming agents. Suspensions, in addition to the elastase inhibitor, may contain suspending agents such as ethoxylated isostearyl alcohols, polyoxyethylene sorbitol and sorbitan esters, microcrystalline cellulose, aluminium metahydroxide, bentonite, agar-agar, and tragacanth and mixtures thereof.

In a suitable embodiment, the pharmaceutical composition is for intramuscular administration. In such an embodiment, a sterile pharmaceutical composition may be especially desirable. A sterile pharmaceutical composition may be obtained, for example, by filtration though sterile filtration membranes.

In a suitable embodiment, the pharmaceutical composition of the present invention may be for sustained release of the elastase inhibitor. Such a pharmaceutical composition may comprise semipermeable matrices of solid hydrophobic polymers containing the elastase inhibitor, wherein the matrices are in the form of shaped articles, films or microcapsules. Examples of sustained-release matrices include polyesters, hydrogels, copolymers of L-glutamic acid and gamma ethyl-L-glutamate, non-degradable ethylene-vinyl acetate degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid.

EXAMPLES 1.1 Elastase Levels are Increased in Dystrophic Muscle

Figure 1:
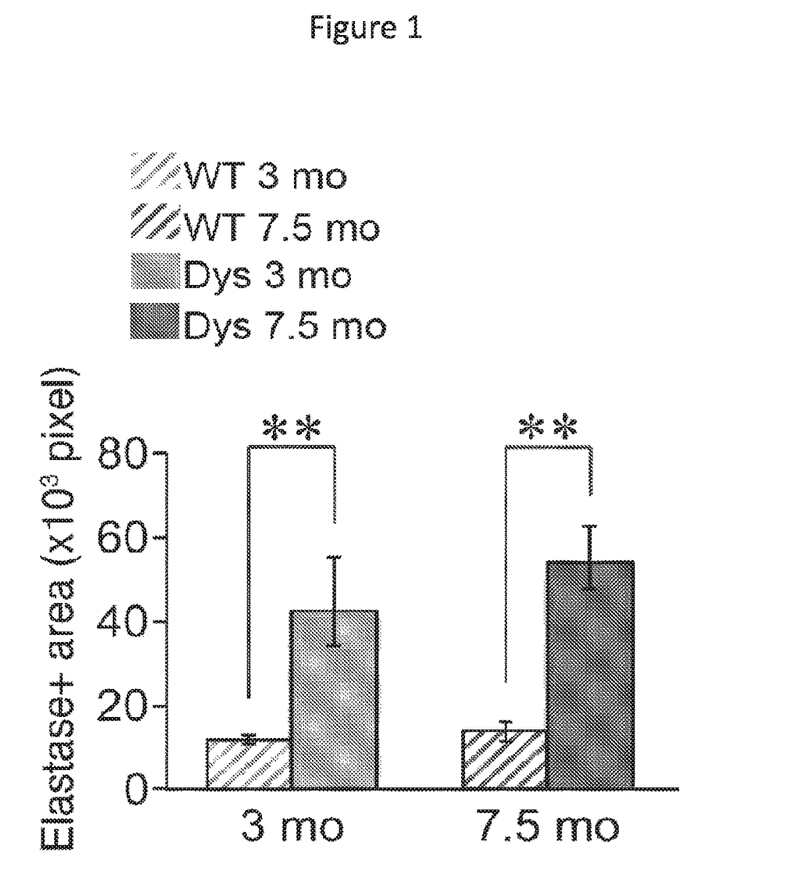
FIG. 1 Shows a graph comparing elastase levels in muscles from wild-type and dystrophic mice.

To study the impact of dystrophy-induced chronic elastase presence on muscle regeneration, we used a mouse model of Duchenne muscular dystrophy, the mdx4cv mouse strain. We collected muscle tissue from mdx4cv mice and sex- and age-matched wild type mice at two ages (3 and 7.5 months) and probed wild type and mdx4cv muscles with an antibody that detects neutrophil elastase. While wild type muscle sections contained elastase only around blood vessels, an accumulation of elastase around and inside muscle fibres was observed in dystrophic muscle sections. When quantified, the amount of elastase staining detected in dystrophic mice of 3 and 7.5 months of age was greater than the amount detected in wild type mice of the same age (FIG. 1). Importantly, the amount of elastase accumulated in dystrophic muscles from 7.5 month-old mice appeared to be greater than the amount detected in younger dystrophic mice, suggesting that elastase accumulates in dystrophic muscle as the disease progresses and muscle loses regenerative capacity.

In order to evaluate the levels of elastase, quadriceps muscles were collected from male dystrophic (mdx4cv strain) and age-matched male wild type mice (C57bl/6J), which share the same background and mdx4cv mice). The muscles were snap-frozen in liquid nitrogen-cooled isopentane on a mounting of optimal cutting temperature compound (OCT). Samples were then cryosectioned, fixed with paraformaldehyde (4% in PBS, pH 7.4) and immunostained to detect neutrophil elastase (with a rabbit anti-elastase antibody from Bioss used at 1:100), laminin (with a rat anti-laminin alpha-2 from Sigma Aldrich used at 1:200) and DNA (with DAPI diluted at 2 µg/mL). Primary antibodies were then detected using AlexaFluor-conjugated secondary antibodies both from Life Technologies and used at 1:500 dilution (anti-rabbit conjugated to Alexa555 and anti-rat conjugated to Alexa488). Sections were imaged on an inverted fluorescence microscope, EVOS-FL, Life Technologies. Quantification of the immunofluorescence data was performed with a bespoke written script for Fiji available at available at (http://fiji.sc). Data from 10 images across 3 biological replicates (N=30) were quantified and plotted as average±the standard error of the mean (FIG. 1).

Figure 7:
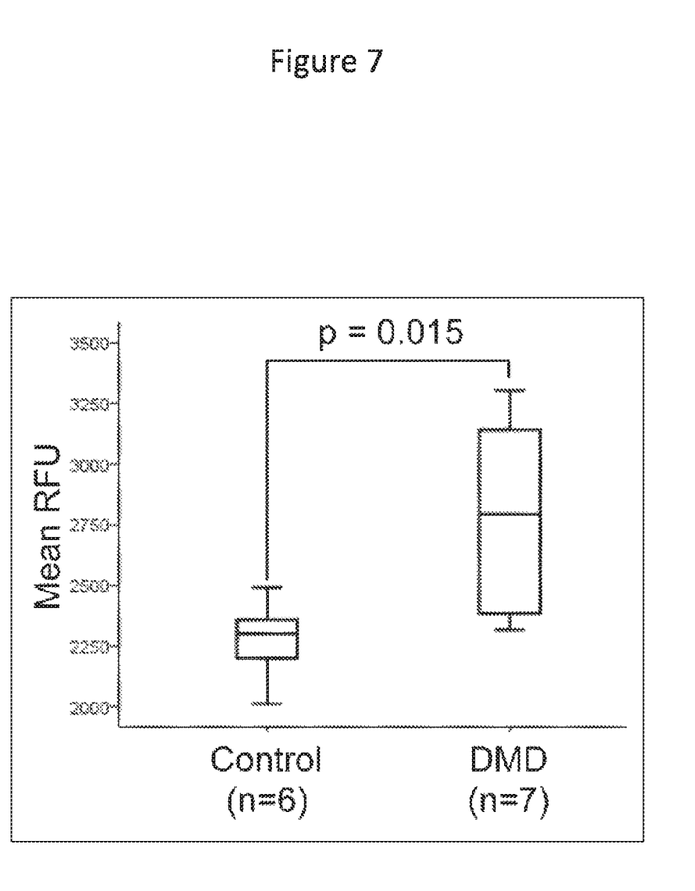
FIG. 7 Shows a graph comparing the levels of elastase activity in the serum of male patients with Duchenne muscular dystrophy and in age-matched healthy male controls.

1.2 Elastase Levels are Increased in the Serum of Duchenne Muscular Dystrophy Patients Elastase levels were assessed in serum samples from patients with Duchenne muscular dystrophy. Serum samples were collected from boys with the diseases and age-matched healthy boys recruited at Alder Hey Children's Hospital, Liverpool, UK. To measure elastase activity in serum, samples were incubated with the fluorigenic peptide Suc-Ala-Ala-Ala-AMC (Peptallova) for three hours at 37° C. and then the amount of fluorescence produced by elastase-mediated cleavage of the fluorigenic peptide was read using a plate reader (Polar Star Optima, BMG Labtech) at 380 nm excitation wavelength and 450 nm emission wavelength. The average emission of three technical replicates for 6 control subjects and 7 Duchenne muscular dystrophy patients were measured. The results (FIG. 7) show that elastase activity was markedly and significantly increased in the blood of boys with Duchenne muscular dystrophy compared to healthy controls. In order to determine whether the results were statically significant, the data were analysed using a two-tailed t-test comparing the averages of healthy controls and patients.

1.3 Effect of Elastase on Myoblast Cell Proliferation and Differentiation

In response to muscle injury or disease (such as muscular dystrophy) locally resident muscle progenitors, which are normally dormant, become activated, proliferate and then differentiate into muscle cells to regenerate the muscle tissue. This process can be recapitulated ex vivo to study the molecular mechanisms that govern it and how regeneration can be impaired or improved. Muscle progenitors are usually derived from the muscle stem cells called satellite cells or, rarely, from non-satellite cell sources, such as pericytes, myoendothelial cells, mesenchymal stem cells, side population cells and myoblasts. When myoblasts are kept in a petri dish in the presence of culture medium (Dulbecco modified Eagle's medium, DMEM) containing 10% of foetal bovine serum they proliferate, dividing approximately twice per day, and eventually they differentiate and fuse to one another generating structures called myotubes, which resemble muscle fibres. This process of differentiation into myotubes can be sped up by switching the growth medium (containing 10% foetal bovine serum) to differentiation medium (containing 3% horse serum).

Elastase is a protease that degrades proteins of the extracellular matrix to which cells adhere in vivo and ex vivo. Cell adhesion is important for cell proliferation and differentiation. Myoblasts cultured in growth medium and exposed to elastase show impaired expansion mostly due to cell detachment, which in turn induces cell death and impairs proliferation in the cells that do not die. When myoblasts are seeded on specific substrates, elastase-induced impairment of proliferation (FIG. 2) and differentiation (FIG. 3) is substrate-dependent manner, with laminin being the substrate that confers the highest sensitivity to elastase treatment.

Figure 2:
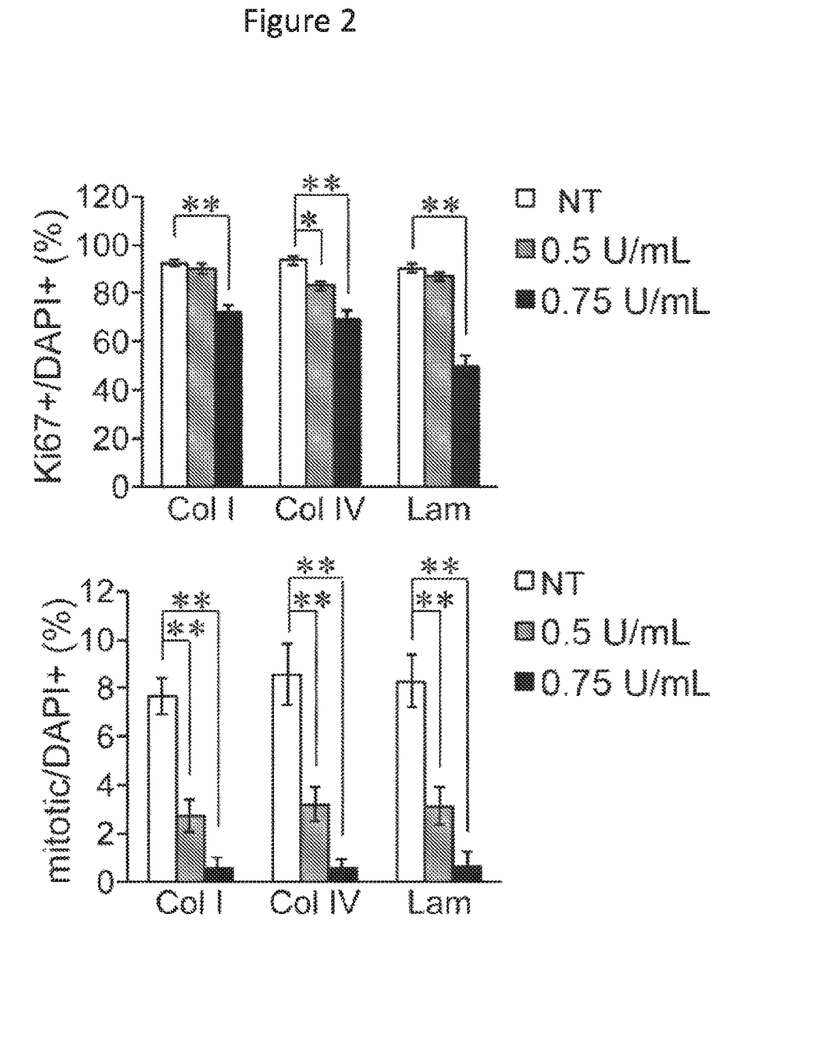
FIG. 2 Shows graphs illustrating the effects of elastase on myoblast proliferation.
Figure 3:
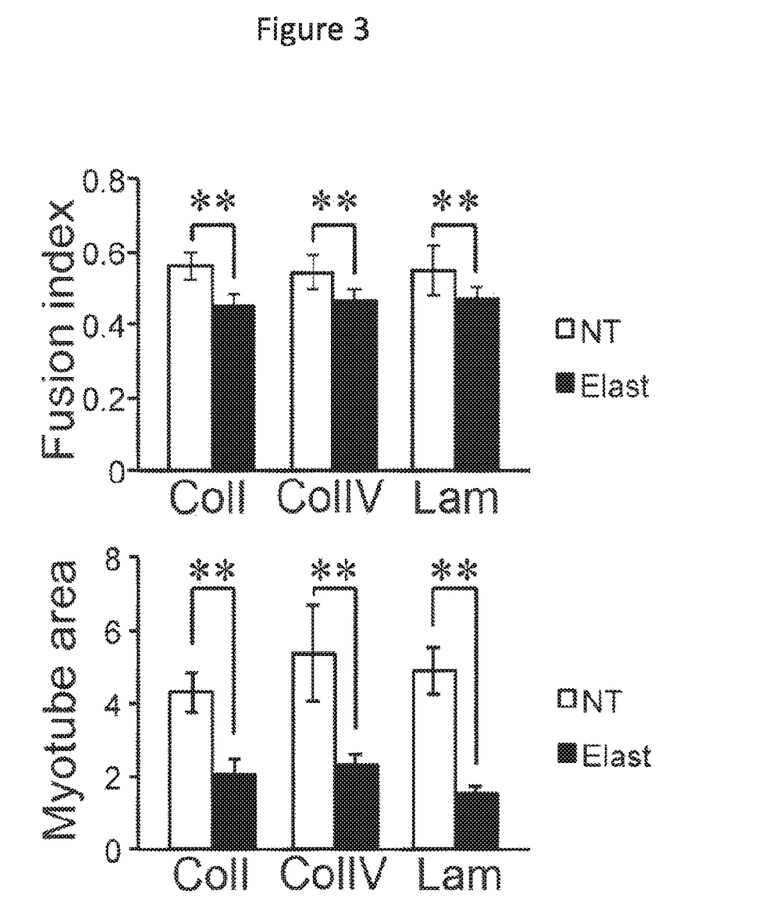
FIG. 3 Shows graphs illustrating the effects of elastase on myoblast differentiation.

In order to determine how elastase impairs myoblast proliferation, myoblasts were seeded at the density of 7,000 cells/well on 12 multi-well plates (Corning) that had been previously coated with either collagen type I, collagen type IV or laminin and grown for 24 hours in growth medium prior to adding purified elastase at either a concentration of 0.5 U/ml or 0.75 u=U/ml. After 24 h in the presence of elastase, the culture medium was removed, the cells fixed with 4% paraformaldehyde and immunostained to detect the proliferation marker Ki67 (using a rabbit-anti Ki67 antibody from Abcam at 1:400) and DNA (using DAPI at 2 μg/mL). Proliferating cells were scored as percentage of Ki67+ cells over the total number of cells (DAPI+) (FIG. 2A). Dividing cells (FIG. 2B) were scored as percentage of Ki67+ cells in mitosis (identified by high Ki67 immunoreactivity and morphology) over the total number of DAPI+ cells. NT=non-treated cultures that did not receive elastase. *=$p<0.05$; =$p<0.01$ In order to determine how elastase impairs myoblast differentiation myoblasts were seeded at a density of 20,000 cells/well on 12-multiwell plates (Corning) that had been previously coated with either collagen type I, collagen type IV or laminin and grown for 24 hours in growth medium prior to switching to differentiating medium (DMEM+3% horse serum) and adding purified elastase at the concentration of 0.15 U/mL. After 4 days of differentiation in the presence of elastase, the culture medium was removed, the cells fixed with 4% paraformaldehyde and immunostained to detect the differentiation marker myosin heavy chain (MyHC, using a mouse monoclonal antibody from Developmental Studies Hybridoma Bank, clone MF20) and DNA (using DAPI at 2 μg/mL). The fusion index (FIG. 3A) was calculated using a bespoke written script for Fiji (available at http://fiji.sc) which calculates the percentage of nuclei present in MyHC+ cells with more than one nucleus over the total number of nuclei present in MyHC+ cells. The total myotube area (FIG. 3B) was calculated using the above-mentioned bespoke written script for Fiji as the total area present in MyHC+ cells with more than one nucleus. NT=non-treated cultures that did not receive elastase. =$p<0.01$.

Figure 4:
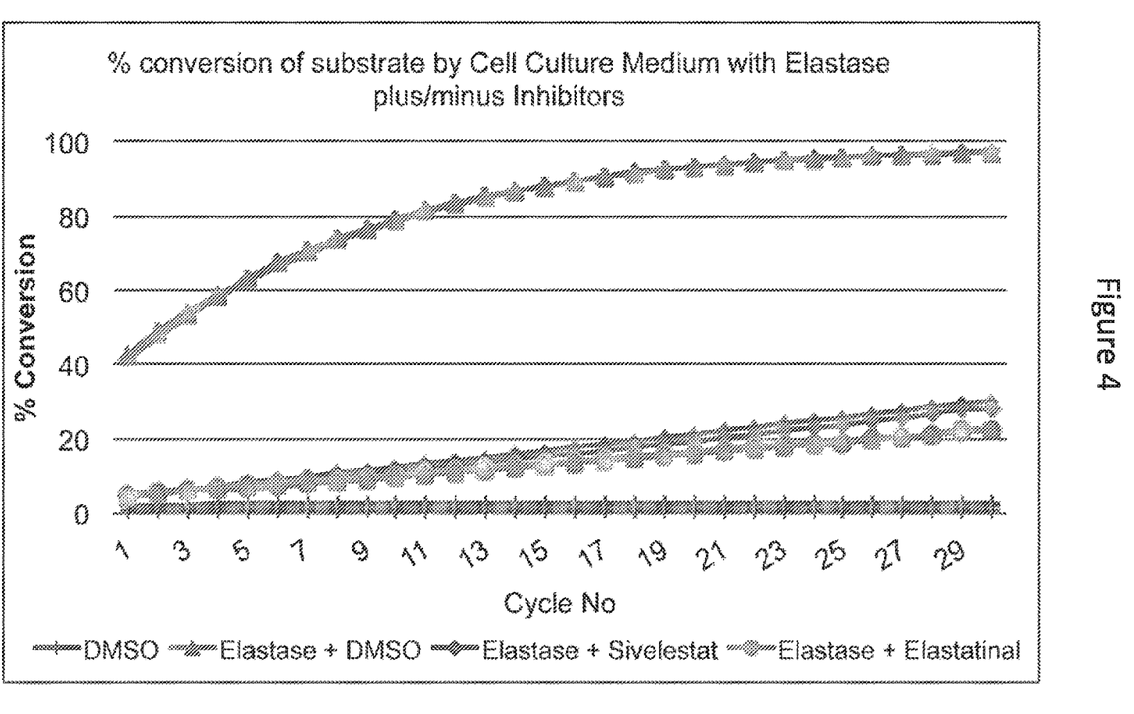
FIG. 4 A graph illustrating the effects of elastase inhibitors on elastase activity in vitro.

1.4 Elastase Inhibitors Inhibit Elastase Activity In Vitro and Protect Elastase-Induced Loss of Muscle Regeneration Ex Vivo Several elastase inhibitors have been developed. To study whether the elastase-induced impairment in muscle regeneration could be reversed ex vivo by elastase inhibitors, we tested different compounds for their efficacy at inhibiting elastase when present in cell culture medium (FIG. 4). Both Sivelestat and Elastatinal (which are selective elastase inhibitors) were very effective at inhibiting elastase in cell culture medium. They reduced elastase activity by approximately 80% when used at the concentration of 100 μM (FIG. 4).

In order to determine the effects of elastase inhibitors on muscle regeneration ex vivo, a fluorescent elastase substrate was incubated with either DMSO or with purified 0.75 U/mL of elastase that had been pre-incubated for 1 hour with either DMSO, or 100 μM Sivelestat, or 100 μM Elastatinal. The percentage of substrate cleavage (substrate conversion to product) was monitored over time by recording product formation every minute for 30 minutes (30 cycles of instrument recording) using a Pierce EZ-Reader. The results are plotted in duplicate and show that both Sivelestat and Elastatinal reduce elastase activity is cell culture medium by approximately 80%.

Figure 5:
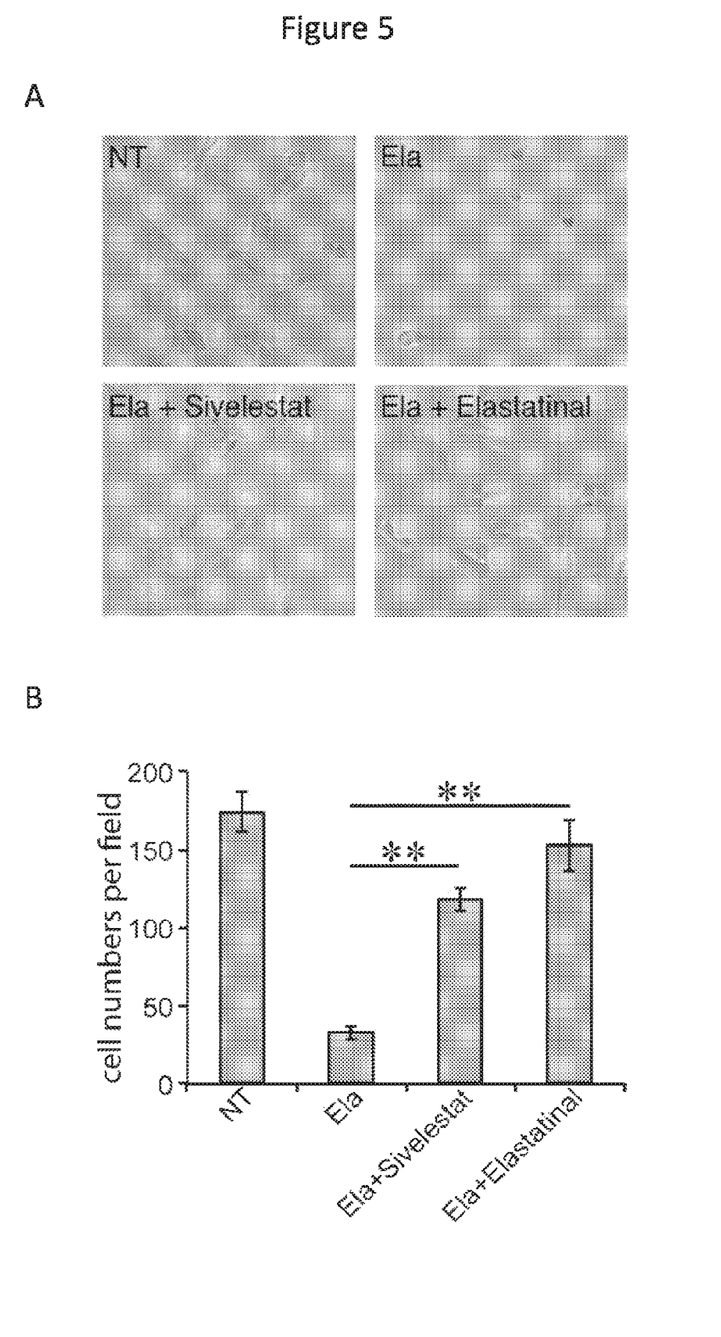
FIG. 5 Illustrates the effects of elastase inhibitors on myoblast cells during muscle regeneration ex vivo. A shows pictures of myoblast cells cultured in the presence of elastase but with or without elastase inhibitors. B shows a graph illustrating the cell number per field of cells cultured in the presence of elastase but with or without elastase inhibitors.

When myoblasts are seeded on uncoated plates and allowed to secrete their own extracellular matrix by culturing them in growth medium for one day, elastase-induced cell loss is still observed 24 hours after plating at an extent that is comparable to the loss observed when myoblasts are seeded on laminin (FIG. 5A and FIG. 5B). However, addition of elastase together with selective inhibitors of elastase activity, such as Sivelestat and Elastatinal, prevents elastase-induced cell loss.

In order to determine the effect of elastase inhibitors on cultures myoblasts, myoblasts were seeded at the density of 7,000 cells/well in 12 multi-well plates (Corning) and grown for 1 day in growth medium. Twenty-four hours after plating, 0.75 U/mL of purified elastase (Sigma Aldrich) were added to the culture medium in the absence (Ela) or presence of either 100 μM Sivelestat (Ela+Sivelestat) or 100 μM Elastatinal (Ela+Elastatinal) and cultured for additional 24 hours. Quantification of total cell numbers per image was done in triplicates and plotted as average±standard error of the mean. NT=non-treated cultures, that received neither elastase nor elastase inhibitors. **=$p<0.01$.

1.5 Elastase Inhibitors Increase the Size of Muscle Fibres

To test whether inhibition of elastase activity promoted muscle regeneration in vivo in dystrophic mice, dystrophic (mdx4cv strain) mice were treated with either the elastase inhibitor Elastatinal (dissolved in saline solution) or saline solution for 12 weeks and muscle fibre size was assayed.

Elastatinal (Enzo Life Sciences) was dissolved in a saline solution (0.9% NaCl) to the concentration of 20 mg/mL and then, either 200 mg/Kg body weight of Elastatinal or an equal volume of saline solution were injected twice a week intraperitoneally into the dystrophic (mdx4cv) mice. After 12 weeks of treatment animals were culled and several muscles dissected, embedded in Optimal Cutting Medium (OCT, Fisher) and frozen in liquid nitrogen-cooled isopentane (Sigma) for histopathological analysis.

Figure 8:
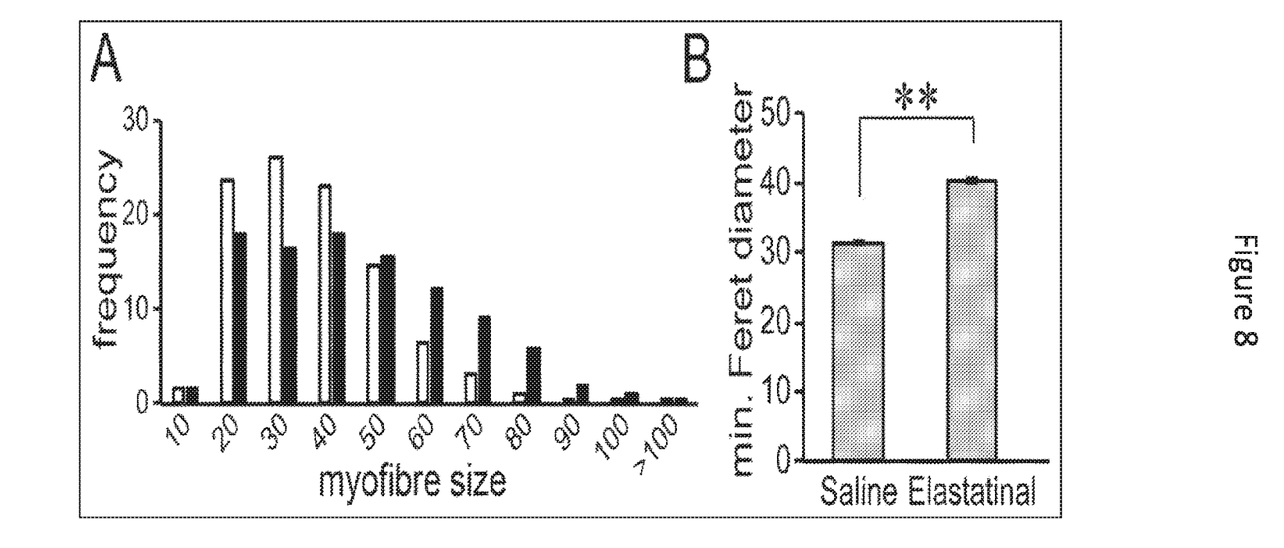
FIG. 8 Illustrates the effects of elastases inhibitors on muscle fibre size. A shows a graph illustrating the frequency of myofibres of various size. B shows the average minimum Feret diameter of myofibres from mice treated with Elastatinal and control mice treated with saline. The error bars show +/−SEM. **=p<0.01

To measure the extent of muscle regeneration, myofibre size was estimated. Sections of the gastrocnemius muscle of either Elastatinal-treated or saline-treated mice were immunostained to detect laminin which marks the periphery of each muscle fibre and then the programme SMASH[1] was used to calculate the minimum Feret diameter as a direct measure of myofibre size. FIG. 8A shows the distribution of minimum Feret diameter values of at least 3,000 fibres measured across three biological replicates in Elastatinal-treated mice (black bars) and saline-treated mice (white bars). FIG. 8B shows the average minimum Feret diameter in Elastatinal-treated mice and saline-treated mice. These day show that elastase inhibitors may promote muscle regeneration through increasing muscle fibre size.

1.6 Elastase Inhibitors Improve Muscle Function In Vivo

To test whether elastase inhibition is effective in counteracting the devastating effects of the muscular dystrophy symptoms, we injected dystrophic (mdx4cv) mice with either 100 mg/Kg body weight of Elastatinal dissolved in sterile saline solution (0.9% $NaCl_2$) or with vehicle (sterile saline solution) alone (n=3) twice a week for 6 weeks then measured the grip strength of all 4 limbs using Kondziela's inverted screen test. Each animal was offered three attempts to reach 90 seconds of grip before falling then the best performance was assigned a score (1 to 6 for every 15 seconds spent on the grid, e.g.: 1-14 seconds=score 1, 15-29 seconds=score 2, etc.). Scores were averaged and plotted as mean±the standard error of the mean.

Figure 6:
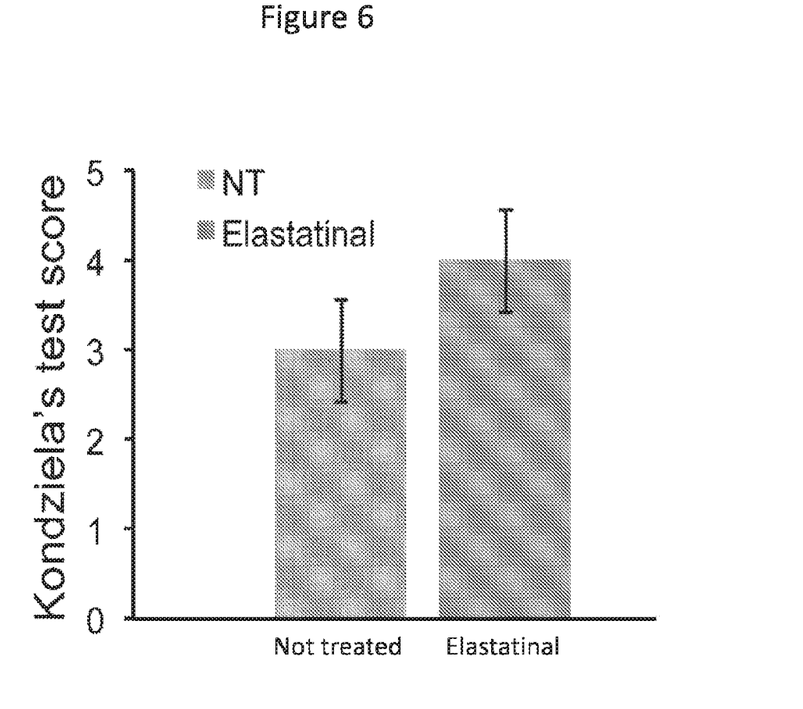
FIG. 6 Shows a graph illustrating the effects of the elastase inhibitor Elastatinal on muscle function in vivo.

Mice treated with Elastatinal showed improved muscle strength (grip strength) compared to mice treated with vehicle only, likely due to improved muscle regeneration achieved upon inhibition of elastase activity (FIG. 6).

Figure 9:
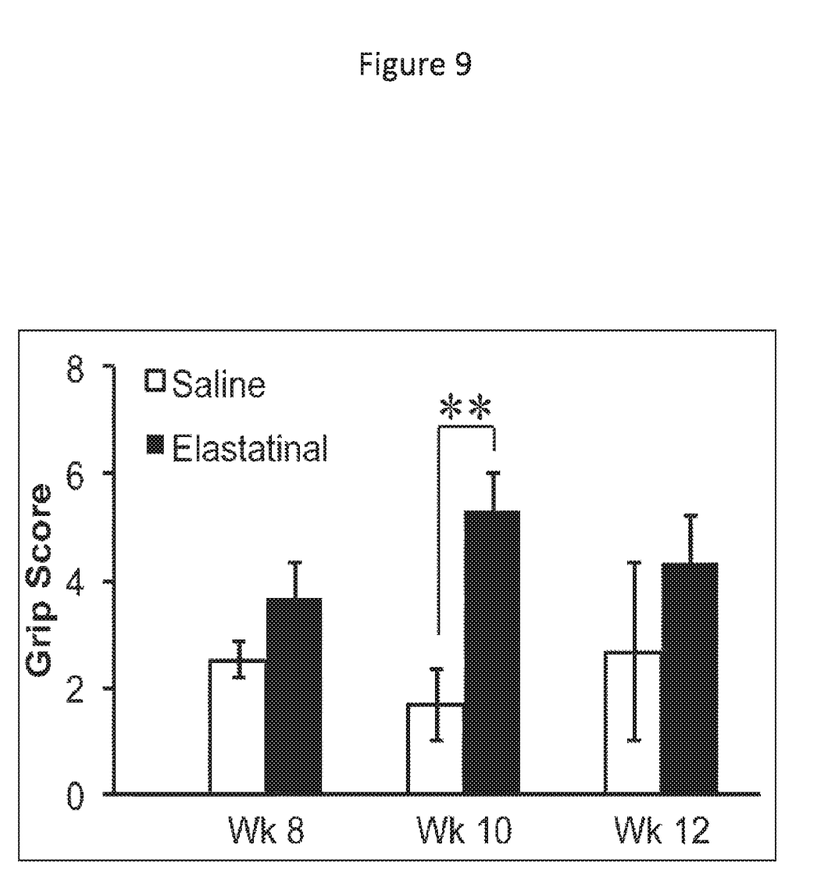
FIG. 9 Shows a graph illustrating the effects of elastase inhibitors on muscle strength measured by grip strength using the Kondziella's inverted screen test. The error bars show +/−SEM. **=p<0.01

In addition to the above mentioned experiment, Elastatinal was dissolved in a saline solution (0.9% NaCl) to a concentration of 20 mg/mL and then either 200 mg/Kg body weight of Elastatinal or an equal volume of saline solution were injected twice a week for 12 weeks intraperitoneally into dystrophic (mdx4cv) mice. At 8, 10 and 12 weeks of treatment, muscle function (grip strength) of the mice was measured using Kondziela's inverted screen test. A 1-6 score was assigned for every 15 seconds of the total time spent by the mouse on the inverted grid such that a score of 6 indicates at least 90 seconds of latency to fall. As shown in FIG. 9, Elastatinal statistically significantly improved grip strength in dystrophic mice. Error bars are S.E.M. **=p<0.01.

1.7 Elastase Inhibitors Decrease Fibrosis and Inflammation

The objective of this experiment was to determine whether elastase inhibitors can reduce inflammation and/or fibrosis. To test this, cross-sections of the gastrocnemius muscle of mice that were treated with either Elastatinal or saline solution were stained with Picrosirius red, or labelled with an anti-CD45 antibody or an anti-laminin antibody. Picrosirius red allows to differentiate between collagen and the rest of the tissue as it stains the collagen a different colour. The anti-CD45 antibody allows the detection of infiltrating leukocytes (which are a marker of inflammation), and the anti-laminin antibody allows the detection of the periphery of myofibres. Both, the amount of fibrosis and the amount of infiltrated CD45+ leukocytes were reduced with Elastatinal treatment, supporting the hypothesis that elastase activity inhibition reduces fibrosis and inflammation.

For this experiment, the mice were treated with an injection of 200 mg/kg of Elastatinal dissolved in a saline solution (0.9% NaCl) to a concentration of 20 mg/mL. Control mice were treated with an equal volume of saline. After 12 weeks, mice were culled and several muscles dissected, embedded in Optima Cutting Medium (OCT, Fisher) and frozen in liquid nitrogen-cooled isopentane (Sigma) for histopathological analysis.

The amount of Picrosirius red staining was quantified by selecting re pixels and quantifying the red area using the ImageJ function "Analyze particles". Averages of 10 technical replicates for each one of 3 biological replicates (N=30) were analysed (FIG. 10 B).

Figure 10:
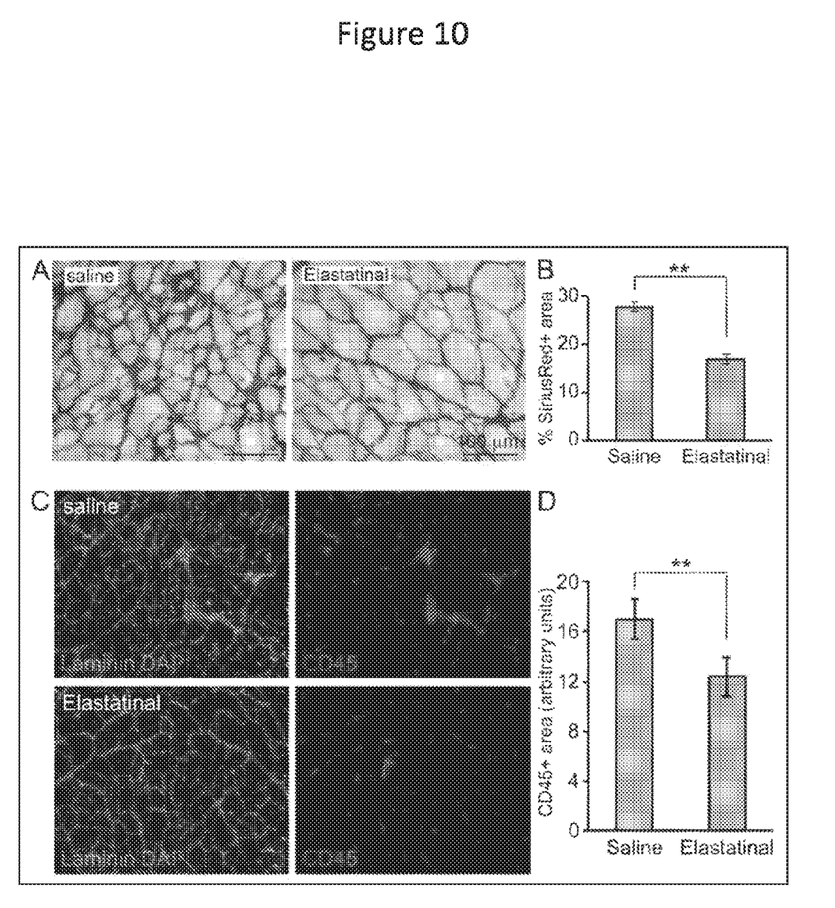
FIG. 10 Illustrates the effects of elastase inhibitors on fibrosis and inflammation. A shows sections of gastrocnemius muscle from saline or Elastatinal treated mice stained with Picrosirius red. Darker staining shows collagen deposits. B shows a graph illustrating the percentage of fibrous tissue in saline or Elastatinal treated mice. C shows sections of gastrocnemius muscle from saline or Elastatinal treated mice stained with either anti-laminin antibodies or anti-CD45 antibodies. D shows a graph illustrating the area of tissue which stained positively with anti-CD45 antibodies.

To measure the extent of inflammation, the numbers of infiltrating leucocyte, recognized by immunostaining for CD45 (BD Biosciences) were scored as percentage of area positive to CD45 immunostaining using a written script for Fiji softwate (available at http://fiji.sc) (FIG. 10 D).

REFERENCES

[1] Smith L R, Barton E R. *SMASH—semi-automatic muscle analysis using segmentation of histology: a MATLAB application*. Skelet Muscle. 2014 Nov. 27; 4:21.

The invention claimed is:

1. A method for promoting muscle regeneration in a subject with a myopathy, wherein the myopathy is muscular dystrophy, and wherein the muscular dystrophy is Duchenne muscular dystrophy, the method comprising providing a subject with a therapeutically effective amount of an elastase inhibitor, wherein the elastase inhibitor is selected from the group consisting of Alvelestat, Elastatinal, Sivelestat.

2. The method according to claim 1, wherein the therapeutically effective amount of the elastase inhibitor is sufficient to protect the regenerative potential of muscle progenitor cells.

3. The method according to claim 1, wherein the promotion of muscle regeneration is for treatment of a myopathy associated with muscle inflammation.

4. The method according to claim 1, wherein the elastase inhibitor is Alvelestat.

5. The method according to claim 4, wherein the therapeutically effective amount is between 10 mg/day and 150 mg/day.

6. The method according to claim 1, wherein the elastase inhibitor is Elastatinal.

7. The method according to claim 6, wherein the therapeutically effective amount is 100 mg/kg or 200 mg/kg.

8. The method according to claim 1, wherein the elastase inhibitor is Sivelestat.

9. The method according to claim 8, wherein the therapeutically effective amount is between 1 mg/kg/day and 10 mg/kg/day.

* * * * *